United States Patent
Fujimaki et al.

(10) Patent No.: US 8,937,721 B2
(45) Date of Patent: Jan. 20, 2015

(54) SENSING DEVICE

(75) Inventors: Makoto Fujimaki, Ibaraki (JP); Shoji Akiyama, Gunma (JP); Kazutoshi Nagata, Gunma (JP)

(73) Assignees: National Institute of Advanced Industrial Science and Technology, Tokyo (JP); Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/980,373

(22) PCT Filed: Nov. 15, 2011

(86) PCT No.: PCT/JP2011/076229
§ 371 (c)(1),
(2), (4) Date: Jul. 18, 2013

(87) PCT Pub. No.: WO2012/098758
PCT Pub. Date: Jul. 26, 2012

(65) Prior Publication Data
US 2013/0293896 A1 Nov. 7, 2013

(30) Foreign Application Priority Data
Jan. 20, 2011 (JP) ................................. 2011-009775

(51) Int. Cl.
*G01N 21/55* (2014.01)

(52) U.S. Cl.
CPC ..................................... *G01N 21/553* (2013.01)
USPC ........................................... 356/445; 356/135

(58) Field of Classification Search
USPC ......... 356/445–448, 928, 929, 135–136, 300; 385/12, 13, 141, 144, 36
See application file for complete search history.

(56) References Cited

U.S. PATENT DOCUMENTS 7,262,866 B2 * 8/2007 Ivarsson .................... 356/630
2006/0001884 A1 1/2006 Tani et al.
(Continued)

FOREIGN PATENT DOCUMENTS

JP 2006-17648 1/2006
JP 2006-502382 1/2006
(Continued)

OTHER PUBLICATIONS

Optical Characterization of Organic Thin Films and Interfaces with Evanescent Waves, Knoll, W., MRS Bulletin, 16, No. 7, Jul. 1991, pp. 29-39.
(Continued)

*Primary Examiner* — Tri T Ton
(74) *Attorney, Agent, or Firm* — Carmody Torrance Sandak & Hennessey LLP

(57) ABSTRACT

A detection device is disclosed which includes: a detection plate in which a silicon layer and a silicon oxide layer are arranged in this order on a silica glass substrate; and optical prism which is optically adhered to a surface of the silica glass substrate of the detection plate, where the surface is not provided with the silicon layer and the silicon oxide layer; a light-irradiation unit configured to irradiate light to the detection plate through the optical prism and arranged so that light is incident on the optical prism with a fixed incident angle; and a light-detection unit configured to detect intensity of reflected light reflected from the detection plate, wherein the detection device detects a change in dielectric constant by detecting a change in property of the reflected light.

11 Claims, 9 Drawing Sheets

(56) References Cited

U.S. PATENT DOCUMENTS

| | | | |
|---|---|---|---|
| 2006/0147147 A1 | 7/2006 | Zourob et al. | |
| 2010/0166359 A1 | 7/2010 | Fujimaki et al. | |
| 2010/0290037 A1* | 11/2010 | Xu et al. | 356/136 |
| 2011/0310383 A1* | 12/2011 | Masson et al. | 356/319 |

FOREIGN PATENT DOCUMENTS

| | | | |
|---|---|---|---|
| JP | 2006-275568 | 10/2006 | |
| JP | 2007-271596 | 10/2007 | |
| JP | 2008-46093 | 2/2008 | |
| JP | 2009-085714 | 4/2009 | |
| JP | 4581135 | 9/2010 | |
| JP | 4595072 | 10/2010 | |
| WO | 2007/029414 | 3/2007 | |
| WO | WO 2010037227 A1 * | 4/2010 | G01N 21/55 |

OTHER PUBLICATIONS

Interfaces and Thin Films as Seen by Bound Electromagnetic Waves, Knoll, W., Annu. Rev., Phys. Chem., 49, 1998, pp. 569-638.

Surface-Plasmon Sensor for Absorption-Sensitivity Enhancement, Kano, H. et al., Applied Optics, vol. 33, No. 22, Aug. 1, 1994, pp. 5166-5170.

Gas Detection by Means of Surface Plasmon Resonance, Nylander, C. et al., Sensors and Actuators, 3, 1982/1983, pp. 79-88.

Novel Silicon Dioxide Sol-Gel Films for Potential Sensor Applications: A Surface Plasmon Resonance Study, Kambhampati, D.K. et al., Langmuir, vol. 17, No. 4, 2001, pp. 1169-1175.

High-Resolution Surface Plasmon Resonance Sensors Based on a Dove Prism, Bolduc, O.R. et al., Talanta, 77, 2009, pp. 1680-1687.

Compact Surface Plasmon Resonance-Transducers with Spectral Readout for Biosensing Applications, Stemmler, I. et al., Sensors and Actuators, B54, 1999, pp. 98-105.

Optical Gas Detection Using Metal Film Enhanced Leaky Mode Spectroscopy, Osterfeld, M. et al., Appl. Phys. Lett., vol. 62, No. 19, May 10, 1993, pp. 2310-2312.

Electro-Optical Waveguide Microscopy, Aust, E.F. et al., J. Appl. Phys., vol. 73, No. 6, Mar. 15, 1993, pp. 2705-2708.

Nanoscale Pore Fabrication for High Sensitivity Waveguide-Mode Biosensors, Fujimaki, M. et al., Microelectronic Engineering, 84, 2007, pp. 1685-1689.

High Sensitivity Sensors Made of Perforated Waveguides, Awazu, K. et al., Optics Express, vol. 15, No. 5, Mar. 5, 2007, pp. 2592-2597.

Highly Sensitive Detection of Processes Occurring Inside Nanoporous Anodic Alumina Templates: A Waveguide Optical Study, Lau, K.H.A. et al., J. Phys. Chem. B, vol. 108, No. 30, 2004, pp. 10812-10818.

Silica-Based Monolithic Sensing Plates for Waveguide-Mode Sensors, Fujimaki, M. et al., Optics Express, vol. 16, No. 9, Apr. 28, 2008, pp. 6408-6416.

The Design of Evanescent-Field-Coupled Waveguide-Mode Sensors, Fujimaki, M. et al., Nanotechnology, 19, 2008, pp. 095503-1-095503-7.

Biomolecular Sensors Utilizing Waveguide Modes Excited by Evanescent Fields, Fujimaki, M. et al., Journal of Microscopy, vol. 229, Pt. 2, 2008, pp. 320-326.

Detection of Colored Nanomaterials Using Evanescent Field-Based Waveguide Sensors, Fujimaki, M. et al., Optics Express, vol. 18, No. 15, Jul. 19, 2010, pp. 15732-15740.

Monitoring the Diffusion of Vapour Molecules in Polymer Films Using SP-Leaky-Mode Spectroscopy, Podgorsek, R.P., Sensors and Actuators, B51, 1998, pp. 146-151.

Optical Sensor Based on Resonant Porous Silicon Structures, Saarinen, J.J. et al., Optics Express, May 16, 2005, vol. 13, No. 10, pp. 3754-3764.

Nanoscale Porous Silicon Waveguide for Label-Free DNA Sensing, Rong, G. et al., Biosensors and Bioelectronics, 23, 2008, pp. 1572-1576.

* cited by examiner

SENSING DEVICE

CROSS REFERENCE TO RELATED APPLICATIONS

This application is a National Stage of International Application No. PCT/JP2011/076229, filed Nov. 15, 2011, which claims priority to Japanese Patent Application No. 2011-009775, filed Jan. 20, 2011, the subject matter which is hereby incorporated by reference.

TECHNICAL FIELD

The present invention relates to a small-sized detection device which can highly sensitively detect adsorption, desorption, access, and change in property of a sample to be detected utilizing a spectral measurement method and an optical waveguide mode.

BACKGROUND ART

As sensors for detecting micromaterials in liquid (e.g., proteins or pathogenic microbes in biosamples; and metal ions or organic molecules in water), sensors utilizing surface plasmon resonance (SPR) have been known (see NPLs 1 to 7). The above sensors utilizing surface plasmon resonance are commonly referred to as SPR (Surface Plasmon Resonance) sensors, and commercially available from many companies such as GE Healthcare, FUJIFILM Corporation, NTT Advanced Technology Corporation, and OPTOQUEST CO., LTD.

FIG. 1 illustrates an exemplary configuration of the most popular SPR sensor 200 in Kretschmann configuration. The SPR sensor 200 has a configuration including the thin metal layer 202 which is formed by vapor-depositing metals such as gold or silver on the glass substrate 201 and the optical prism 203 which is adhered to a surface of the glass substrate 201 opposite to a surface on which the thin metal layer 202 is formed; and has a function of polarizing laser light irradiated from the light source 204 by the polarizing plate 205 and irradiating the polarized light to the glass substrate 201 through the optical prism 203. The incident light 210A is made incident under a condition at which total reflection occurs. A surface plasmon resonance appears at a certain incident angle by an evanescent wave formed when the incident light 210A is transmitted to a metal surface-side. When the surface plasmon resonance appears, the evanescent wave is absorbed by surface plasmon, therefore, reflected light near the incident angle is significantly decreased in intensity. A condition under which the surface plasmon resonance appears varies depending on the dielectric constant in the proximity of the surface of the thin metal layer 202. Thus, when a sample to be detected binds to or adsorbs on the surface of the thin metal layer 202 to thereby change the dielectric constant, the reflection property of the incident light 210A also changes. Accordingly, the sample to be detected can be detected by monitoring, using the detector 206, a change in intensity of the reflected light 210B reflected from the thin metal layer 202.

The SPR sensor 200 detects the change in the dielectric constant in the proximity of the surface of the thin metal layer 202, so that it also can detect whether a certain substance accesses a metal surface (access), whether a substance which has been adhered to a metal surface desorbs from the metal surface, or whether a substance which has been present at a metal surface changes in property, in addition to adsorption of a sample to be detected.

However, in order to detect a property of a sample to be detected at a surface of the thin metal layer 202, it is necessary to move an optical system including the light source 204, alter an angle θ at which the incident light 210A is introduced to the thin metal layer 202, and then appropriately monitor the reflected light 210B by the detector 206, which causes complexity in configuration of the optical system and increases in size of a detection device.

A spectral measurement method has been reported in which an optical system in a SPR sensor is simplified and small-sized (see NPLs 6 and 7). FIG. 2 illustrates a schematic view of the SPR sensor 300 provided with the optical system which is employed in NPL 6. The incident light 310A is directed from the light source 301 to in front of the optical prism 303 via the optical fiber 302A, made into collimated light by the collimator lens 304, and then p-polarized by the polarizing plate 305, followed by being incident on the optical prism 303. This incident light 310A is irradiated to the thin metal layer 307 on the glass substrate 306, the glass substrate being arranged so as to adhere to the optical prism 303; and directed through the condensing lens 308 to the detector 309 via the optical fiber 302B, as the reflected light 310B which is reflected from the thin metal layer 307. Here, the photodetector 309 is provided with the spectroscope 309A, and has a function of measuring the reflection spectrum of the reflected light 310B. The SPR sensor 300 is similar to the SPR sensor 200 in that a change in the dielectric constant can be detected by measuring the reflection spectrum caused by the change in the dielectric constant in the proximity of a surface of the thin metal layer 307. However, it is difficult from the SPR sensor 200 in that the reflected light 310B is wavelength-resolved, and then measured for the spectrum thereof without changing the incident angle 310A to the thin metal layer by moving the optical system, which allows the optical system to be simplified and small-sized.

However, the SPR sensor utilizing the surface plasmon resonance has disadvantages in stability and sensitivity of measurements. Therefore, there is need to provide a highly stable and highly sensitive detection device.

An optical waveguide mode sensor has been reported which is similar to the SPR sensor in configuration and which also detects adsorption or change in the dielectric constant of a substance at a detecting surface of the sensor (see NPLs 1, 2, 8 to 19, and PTLs 1 to 5).

The optical waveguide mode sensor has been known to be capable of using an optical system equivalent to any optical systems used in the SPR sensors. FIG. 3 illustrates the optical waveguide mode sensor 400 having a similar configuration to the Kretschmann configuration. The optical waveguide mode sensor 400 uses the detection plate 401 consisting of the transparent substrate 401a (e.g., plate glass), the reflection layer 401b composed of a metal layer or a semiconductor layer coated on the transparent substrate, and the transparent optical waveguide layer 401c formed on the reflection layer 401b. Further, the optical prism 402 is adhered, via a refractive index-matching oil, to the surface of the detection plate 401 opposite to the surface on which the transparent optical waveguide layer 401c is formed. Light is irradiated from the light source 403, polarized by the polarizing plate 404, and then irradiated to the detection plate 401 through the optical prism 402. The incident light 410A is incident on the detection plate 401 under a condition at which total reflection occurs. Upon coupling of the incident light 410A with the optical waveguide mode (may be referred to as leaky mode) at a certain incident angle, the optical waveguide mode is excited to thereby significantly change the reflected light in intensity near the incident angle. Such a condition for exciting optical waveguide mode varies depending on the dielectric constant in the proximity of the surface of the transparent optical waveguide layer 401c. Therefore, the reflected light 410B changes in intensity when a substance is adsorbed onto, access, desorbs from, or changes in property on a surface of the transparent optical waveguide layer 401c. These phenomena such as adsorption, access, desorption, or change in property on the surface of the transparent optical waveguide layer 401c can be detected by measuring the change in intensity with the detector 405.

As disclosed in NPL 13 or PTL 5, a detection plate ($SiO_2$/Si/$SiO_2$ detection plate) used in the optical waveguide mode sensor has been proposed which includes silica glass (may be referred to as $SiO_2$ glass, silica, or quartz glass) serving as a substrate, a silicon (Si) layer placed on the silica glass, and a silicon oxide (including thermal oxidized $SiO_2$ or silica glass) layer placed on the silicon (Si) layer, and a highly sensitive and highly stable sensor can be achieved by using the detection plate.

CITATION LIST

Patent Literature

PTL 1: Japanese Patent (JP-B) No. 4581135
PTL 2: JP-B No. 4595072
PTL 3: Japanese Patent Application Laid-Open (JP-A) No. 2007-271596
PTL 4: JP-A No. 2008-46093
PTL 5: JP-A No. 2009-85714

Non-Patent Literature

NPL 1: W. Knoll, MRS Bulletin 16, pp. 29-39 (1991)
NPL 2: W. Knoll, Annu. Rev. Phys. Chem. 49, pp. 569-638 (1998)
NPL 3: H. Kano and S. Kawata, Appl. Opt. 33, pp. 5166-5170 (1994)
NPL 4: C. Nylander, B. Liedberg, and T. Lind, Sensor. Actuat. 3, pp. 79-88 (1982/83)
NPL 5: K. Kambhampati, T. A. M. Jakob, J. W. Robertson, M. Cai, J. E. Pemberton, and W. Knoll, Langmuir 17, pp. 1169-1175 (2001)
NPL 6: O. R. Bolduc, L. S. Live, and J. F. Masson, Talanta 77, pp. 1680-1687 (2009)
NPL 7: I. Stammler, A. Brecht, and G. Gauglitz, Sensor. Actuat. B54, pp 98-105 (1999)
NPL 8: M. Osterfeld, H. Franke, and C. Feger, Appl. Phys. Lett. 62, pp. 2310-2312 (1993)
NPL 9: E. F. Aust and W. Knoll, J. Appl. Phys. 73, p. 2705 (1993)
NPL 10: M. Fujimaki, C. Rockstuhl, X. Wang, K. Awazu, J. Tominaga, T. Ikeda, Y. Ohki, and T. Komatsubara, Microelectronic Engineering 84, pp. 1685-1689 (2007)
NPL 11: K. Awazu, C. Rockstuhl, M. Fujimaki, N. Fukuda, J. Tominaga, T. Komatsubara, T. Ikeda, and Y. Ohki, Optics Express 15, pp. 2592-2597 (2007)
NPL 12: K. H. A. Lau, L. S. Tan, K. Tamada, M. S. Sander, and W. Knoll, J. Phys. Chem. B108, pp. 10812 (2004)
NPL 13: M. Fujimaki, C. Rockstuhl, X. Wang, K. Awazu, J. Tominaga, Y. Koganezawa, Y. Ohki, and T. Komatsubara, Optics Express 16, pp. 6408-6416 (2008)
NPL 14: M. Fujimaki, C. Rockstuhl, X. Wang, K. Awazu, J. Tominaga, N. Fukuda, Y. Koganezawa, and Y. Ohki, Nanotechnology 19, pp. 095503-1-095503-7 (2008)
NPL 15: M. Fujimaki, C. Rockstuhl, X. Wang, K. Awazu, J. Tominaga, T. Ikeda, Y. Koganezawa, and Y. Ohki, J. Microscopy 229, pp. 320-326 (2008)
NPL 16: M. Fujimaki, K. Nomura, K. Sato, T. Kato, S. C. B. Gopinath, X. Wang, K. Awazu, and Y. Ohki, Optics Express 18, pp. 15732-15740 (2010)
NPL 17: R. P. Podgorsek, H. Franke, J. Woods, and S. Morrill, Sensor. Actuat. B51 pp. 146-151 (1998)
NPL 18: J. J. Saarinen, S. M. Weiss, P. M. Fauchet, and J. E. Sipe, Opt. Express 13, pp. 3754-3764 (2005)
NPL 19: G. Rong, A. Najmaie, J. E. Sipe, and S. M. Weiss, Biosens. Bioelectron. 23, pp. 1572-1576 (2008)

SUMMARY OF INVENTION

Technical Problem

A high-performance and small-sized sensor can be achieved by adapting the spectral measurement method which has been reported in the SPR sensor to the optical waveguide mode sensor.

However, although the SPR sensor is similar to the optical waveguide mode sensor in optical setup, conditions for exciting SPR are completely different from that of the optical waveguide mode. Therefore, a difference between a condition for exciting SPR in conventional SPR sensors and a condition for exciting optical waveguide mode in optical waveguide mode sensors is needed to be complemented.

Regarding the above, wavelengths being capable of exciting SPR are limited to a certain wavelength range depending on metal materials used. Also, the conditions for exciting SPR depend on the complex refractive index of each of materials such as metal materials, materials of substrates, and materials of optical prisms. For example, an optimum value of the incident angle of incident light upon being incident on a metal material surface through a substrate is determined uniquely depending on the materials used.

On the other hand, an excitation wavelength of the optical waveguide mode in the optical waveguide mode sensor using the $SiO_2$/Si/$SiO_2$ detection plate is greatly dependent on the thickness of the silicon layer or the thickness of the silicon oxide layer. Based on the above-described property, the excitation wavelength range of the optical waveguide mode can be freely set by controlling the thicknesses of these layers as long as it falls within a ultraviolet to near-infrared region. In the case of the optical waveguide mode sensor, dissimilar to the SPR sensor, an optimum value of the incident angle from the substrate to the optical waveguide layer in the detection plate depends on the thickness of the silicon layer and the silicon oxide layer, as well as the wavelength of incident light. Therefore, the optical waveguide mode sensor is more advantageous than the SPR sensor in that the optical waveguide mode sensor has a great flexibility in design.

In order to adapt the spectral measurement method to the optical waveguide mode sensor by using the $SiO_2$/Si/$SiO_2$ detection plate, a difference between a condition for exciting SPR in the SPR sensors and a condition for exciting optical waveguide mode in optical wave guide mode sensors can be complemented by setting the angle of the optical prism, to which the light from the light source is irradiated, to a certain angle to thereby allow the incident light to be optimum for exciting optical waveguide mode.

The present invention aims to solve the above existing problems and novel technical problems raised by attempting to provide a detection device using the optical waveguide mode sensor to which the spectral measurement method is adapted; and achieve the following objects. That is, the present invention aims to provide a small-sized, stable, and highly sensitive detection device by complementing a difference between a condition for exciting SPR in SPR sensors and a condition for exciting optical waveguide mode in optical waveguide mode sensors in order to achieve a detection device using the optical waveguide mode sensor to which the spectral measurement method is adapted.

Solution to Problem

Means for solving the above problems are as follows.
<1> A detection device including:
a detection plate in which a silicon layer and a silicon oxide layer are arranged in this order on a silica glass substrate;
an optical prism which is optically adhered to a surface of the silica glass substrate of the detection plate, where the surface is not provided with the silicon layer and the silicon oxide layer;
a light-irradiation unit configured to irradiate light to the detection plate through the optical prism and arranged so that light is incident on the optical prism with a fixed incident angle; and
a light-detection unit configured to detect intensity of reflected light reflected from the detection plate,
wherein the detection device detects a change in dielectric constant in the proximity of the surface of the silicon oxide layer of the detection plate by detecting a change in property of the reflected light, and
wherein in the optical prism, an angle between an incident surface on which light irradiated from the light-irradiation unit is incident and an adhesion surface which adheres to the detection plate is 43° or less.
<2> The detection device according to <1>, wherein the light-irradiation unit irradiates light in parallel with an in-plane direction of the adhesion surface.
<3> The detection device according to <1> or <2>, wherein the silicon layer is formed from single crystal silicon.
<4> The detection device according to any one of <1> to <3>, wherein an interface roughness between the silicon layer and the silicon oxide layer is 0.5 nm or less as a RMS value.
<5> The detection device according to any one of <1> to <4>, wherein the light-irradiation unit includes a light source, a collimator configured to collimate light irradiated from the light source to form collimated light, and a polarizing plate configured to polarize the collimated light into s-polarized light, and wherein the light-irradiation unit irradiates the s-polarized light to the detection plate through the optical prism.
<6> The detection device according to any one of <1> to <5>, wherein the light-detection unit includes a spectroscope configured to spectroscopically disperse and detect the reflected light.
<7> The detection device according to any one of <1> to <6>, wherein the optical prism has an exit surface which forms the same angle to the adhesion surface as that of the incident surface.
<8> The detection device according to any one of <1> to <7>, wherein the optical prism is formed from silica glass having the same refractive index as that of the silica glass substrate.
<9> The detection device according to any one of <1> to <8>, wherein the optical prism and the detection plate are integrally formed.
<10> The detection device according to any one of <1> to <9>, wherein any of adsorption, desorption, access, or change in property of a substance in the proximity of a surface of the silicon oxide layer is detected as a change in dielectric constant.

Advantageous Effects of Invention

According to the present invention, there can be solved the above existing problems and novel technical problems raised by attempting to provide a detection device using the optical waveguide mode sensor to which the spectral measurement method is adapted; and there can be provided a small-sized, stable, and highly sensitive detection device by complementing a difference between a condition for exciting SPR in conventional SPR sensors and a condition for exciting optical waveguide mode in optical waveguide mode sensors in order to achieve a detection device using the optical waveguide mode sensor to which the spectral measurement method is adapted.

Figure 1:
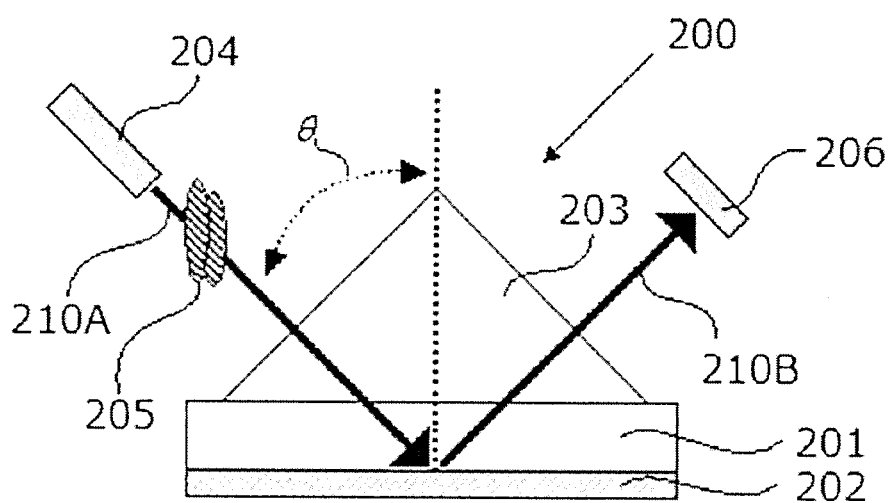
FIG. 1 illustrates an explanatory view of an exemplary optical configuration of the SPR sensor 200 utilizing surface plasmon resonance according to a related art.
Figure 2:
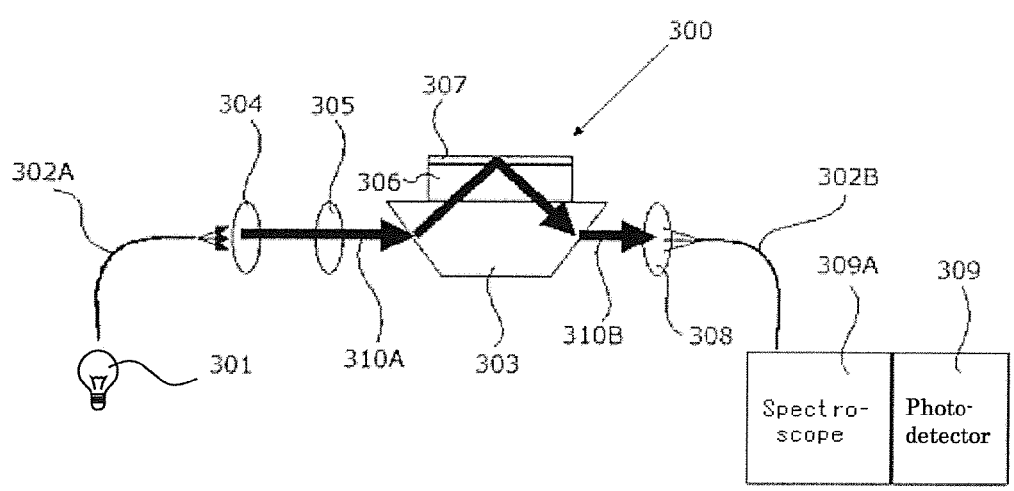
FIG. 2 illustrates an explanatory view of an exemplary optical configuration of the SPR sensor 300 utilizing surface plasmon resonance according to a related art.
Figure 3:
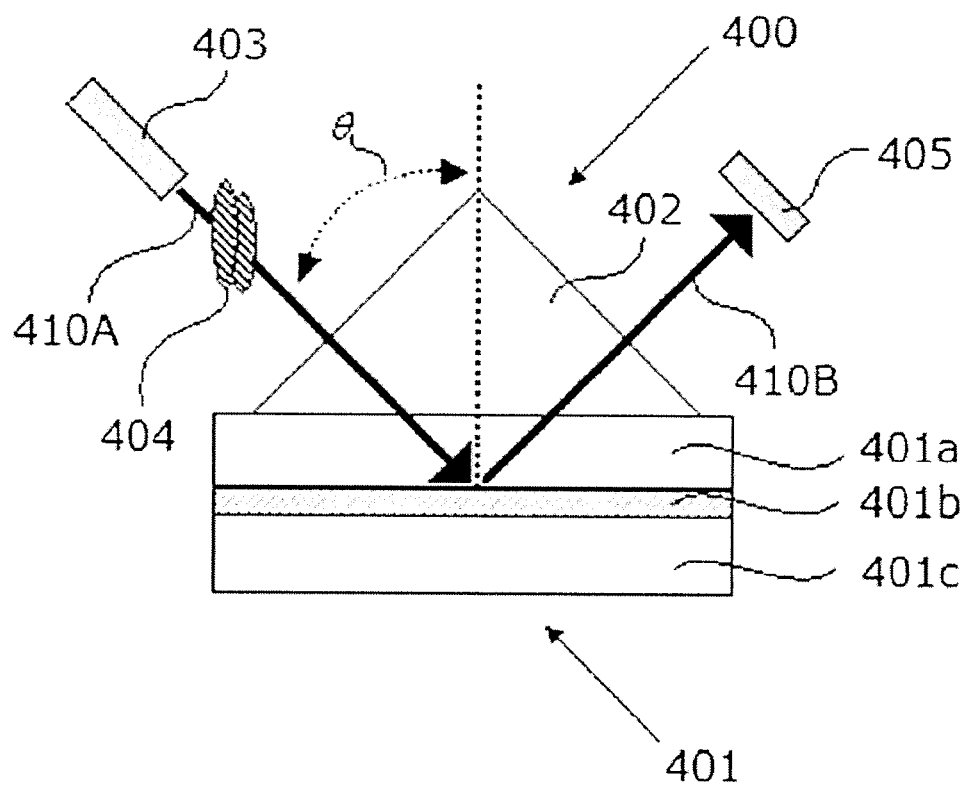
FIG. 3 illustrates an explanatory view of an exemplary optical configuration of the optical waveguide mode sensor 400 according to a related art.

DESCRIPTION OF EMBODIMENTS (Detection Device)
A detection device of the present invention includes a detection plate, an optical prism, a light-irradiation unit, and a light-detection unit.

<Detection Plate>

The detection plate includes a silica glass substrate, and a silicon layer and a silicon oxide layer which are arranged in this order on the silica glass substrate.

The silica glass substrate is not particularly limited and may be appropriately selected depending on the intended purpose, as long as it is a glass material formed of silica glass. For example, the silica glass substrate may be appropriately selected from glass materials referred to as, for example, $SiO_2$ glass, silica or quartz glass.

The material for forming the silicon layer is not particularly limited and may be appropriately selected depending on the intended purpose. Examples thereof include materials mainly containing silicon such as single crystal silicon, amorphous silicon, and polysilicon. Among them, single crystal silicon is preferred from the viewpoint of optical and structural uniformity.

The silicon oxide layer is not particularly limited and may be appropriately selected depending on the intended purpose, as long as it can serve as an optical waveguide layer. Examples thereof include silicon oxides such as thermal-oxidized silicon ($SiO_2$) or silica glass.

The thickness of the silica glass substrate is not particularly limited and may be appropriately selected depending on the intended purpose. However, it is preferably 0.5 mm to 3 mm from the viewpoint of easiness in handling.

The thickness of the silicon layer is not particularly limited and may be appropriately selected depending on the intended purpose, as long as an optical waveguide mode can be excited. However, it is preferably 10 nm to 1 μm from the viewpoint of being capable of exciting an optical waveguide mode in a wavelength range from near-ultraviolet to near-infrared, more preferably 500 nm or less from the viewpoint of easiness in manufacturing.

The thickness of the silicon oxide layer is not particularly limited and may be appropriately selected depending on the intended purpose. However, it is preferably 200 nm to 800 nm from the viewpoints of a function as an optical waveguide and easiness in manufacturing.

The interface roughness between the silicon layer and the silicon oxide layer is not particularly limited and may be appropriately selected depending on the intended purpose. However, it is preferably 0.5 nm or less, ideally 0 nm as a RMS (Root Mean Square) value from the viewpoint of suppressing light-scattering.

Further, detection sensitivity can be improved by forming nano-pores on a surface of the silicon oxide layer.

Figure 4:
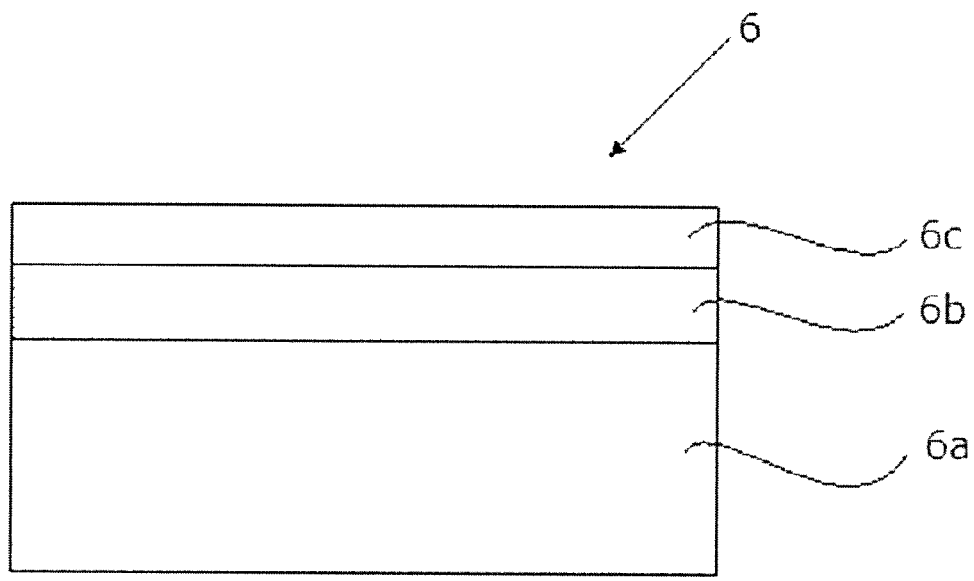
FIG. 4 illustrates an explanatory view of a cross-section structure of a detection plate used in a detection device according to the present invention.

FIG. 4 illustrates a cross-section structure of the detection plate. As shown in FIG. 4, in the detection plate 6, the silicon layer 6b and the silicon oxide layer 6c are arranged in this order on the silica glass substrate 6a. The below-described optical prism is adhered onto a surface of the silica glass substrate 6a opposite to a surface on which the silicon oxide layer 6c is formed.

<Optical Prism>

The optical prism is optically adhered to a surface of the silica glass substrate of the detection plate, where the surface is not provided with the silicon layer and the silicon oxide layer.

The material of the optical prism is not particularly limited and may be appropriately selected depending on the intended purpose, but is preferably silica glass having the same refractive index as that of the silica glass substrate from the viewpoint of preventing reflection or refraction of light at an interface with the detection plate.

The detection device of the present invention is mainly characterized in that an angle between an incident surface on which light irradiated from the light-irradiation unit is incident and an adhesion surface which adheres to the detection plate (i.e., the angle shown as a in the drawings) is 43° or less. As such, a difference between a condition for exciting SPR in conventional SPR sensors and a condition for exciting optical waveguide mode in optical waveguide mode sensors can be complemented.

Figure 5:
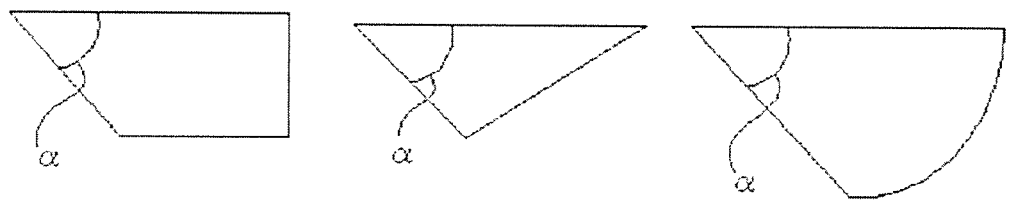
FIG. 5 illustrates an explanatory view of a shape of an optical prism used in a detection device according to the present invention.

Therefore, the shape of the optical prism is not particularly limited and may be appropriately selected depending on the intended purpose, as long as the optical prism has the angle which falls within the above-described range. For example, the optical prism has any of shapes shown in FIG. 5. Notably, the tip of the angle may be rounded by polishing.

Figure 6:
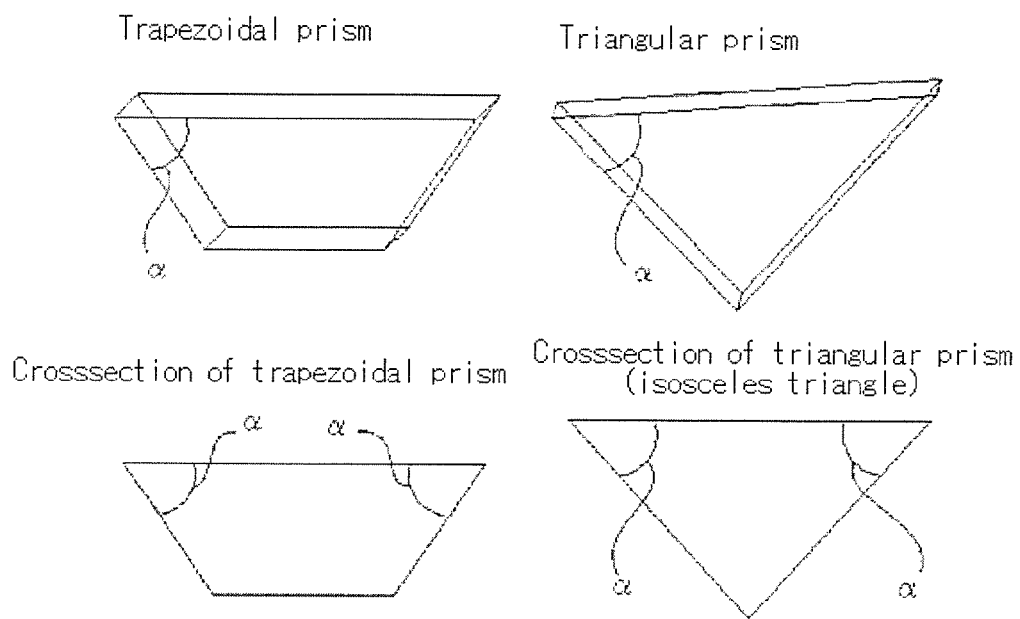
FIG. 6 illustrates another explanatory view of a shape of an optical prism used in a detection device according to the present invention.

Preferred examples of the optical prism include prisms having a trapezoidal cross-section or an isosceles triangular cross-section as shown in FIG. 6. In the case of the above optical prisms, the optical prism has an exit surface which forms the same angle to the adhesion surface which adheres to the detection plate as that of the incident surface on which light irradiated from the light-irradiation unit is incident (i.e., the angle α in FIG. 6), so that the light-irradiation unit and the light-detection unit can be optically symmetrically configured about the optical prism, which allows the detection device to be smaller-sized and to have a simpler configuration design.

A method for allowing the optical prism to adhere to the detection plate is not particularly limited and may be appropriately selected depending on the intended purpose. Preferably, the optical prism is adhered to the detection plate so as to be optically continuous by filling a gap between the detection plate and the optical prism with a refractive index-matching oil or a refractive index-matching polymer sheet.

The detection plate and the optical prism may be integrally formed from the viewpoint of obtaining optical continuity more easily.

In this case, the silica glass substrate in the detection plate can be polished so as to have a prism-like shape in order to attain the same effect.

Figure 7:
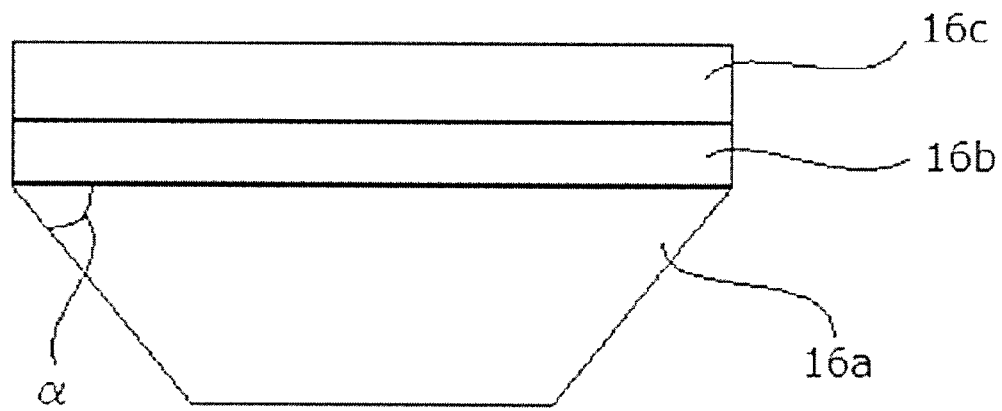
FIG. 7 illustrates an explanatory view of a cross-section structure of an optical prism and a detection plate, which are integrally formed, used in a detection device according to the present invention.

FIG. 7 illustrates an example in which the detection plate and the optical prism are integrally formed. In this case, there is used, as the detection plate and the optical prism, a chip in which the silicon layer 16b and the silicon oxide layer 16c are arranged in this order on the prismatic silica glass substrate 16a which is formed by processing a silica glass substrate into an optical prism-like shape. Here, an angle (α in this figure) between a light incident surface of the prismatic silica glass substrate 16a and an adhesion surface which adheres to the detection plate (i.e., the silicon layer 16b) is 43° or less.

<Light-Irradiation Unit>

The light-irradiation unit irradiates light to the detection plate through the optical prism and is arranged so that light is incident on the optical prism with a fixed incident angle.

The light-irradiation unit is not particularly limited and may be appropriately selected depending on the intended purpose, but preferably irradiates light in parallel with an in-plane direction of the adhesion surface. Such a configuration of the optical system in the light-irradiation unit can achieve a smaller-sized and simpler optical system.

Suitable configuration examples of the light-irradiation unit include those including a light source, a collimator configured to collimate light irradiated from the light source to form collimated light, and a polarizing plate configured to polarize the collimated light into s-polarized light; and being configured to irradiate the s-polarized light to the detection plate through the optical prism. Such a configuration of the light-irradiation unit can achieve an optical system capable of irradiating light to the optical prism with an appropriate incident angle and of making more highly sensitive detecting.

The light source is preferably a white lamp, LED, or LD from the viewpoint of performing a spectral measurement. A p-polarizing plate may be used instead of the s-polarizing plate. However, the s-polarizing plate can achieve higher sensitivity.

Notably, other members may be included in the light-irradiation unit such as optical members (e.g., an optical fiber for directing light irradiated from the light source to the collimator).

<Light-Detection Unit>

The light-detection unit has a function of detecting the intensity of reflected light reflected from the detection plate. The detection device of the present invention detects a change in the dielectric constant in the proximity of a surface of the silicon oxide layer in the detection plate by detecting a change in property of the reflected light.

The light-detection unit is not particularly limited and may be appropriately selected depending on the intended purpose, as long as it has the above-described function. For example, the light-detection unit may include a spectroscope and a photodetector; and, if necessary, further include other units such as a condensing lens or an optical fiber. The condensing lens and the optical fiber can provide flexibility in optical configurations.

The photodetector is not particularly limited and may be appropriately selected depending on the intended purpose. Examples thereof include a device for measuring the intensity of reflected light exited from the optical prism such as a CCD array, a photodiode array, or a photomultiplier. The above device can detect the intensity of the reflected light within a certain wavelength range or the reflection spectrum based on the intensity of the reflected light at every wavelength acquired with the spectroscope.

Figure 8:
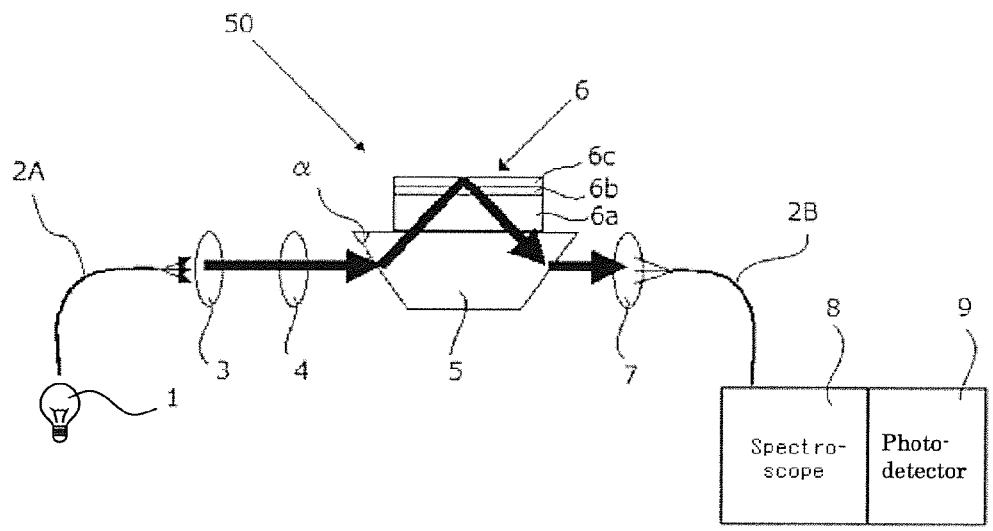
FIG. 8 illustrates an explanatory schematic view of a detection device according to an embodiment of the present invention.

The detection device 50 according to one embodiment of the present invention is shown in FIG. 8. As shown in FIG. 8, the light-irradiation unit includes the light source 1, the optical fiber 2A, the collimator lens 3 and the polarizing plate 4. Light from the light source 1 is incident to the optical fiber 2A and then directed to a position from which light can easily be incident on the optical prism 5. The collimator lens 3 arranged forward of the optical fiber 2A is set so as to make exit light from the optical fiber 2A to be collimated light. The exit light is polarized to a desired polarized state by the polarizing plate 4 and then incident on the optical prism 5.

The light which has been indent on the optical prism 5 is reflected by the detection plate 6 and then exits from the optical prism 5 as reflected light, followed by being concentrated by the condensing lens 7 and being introduced into the optical fiber 2B to thereby be capable of measuring the reflection intensity or the reflection spectrum by the spectroscope 8 and the photodetector 9. The detection plate 6 has a configuration in which the silicon layer 6b and the silicon oxide layer 6c are arranged in this order on the silica glass substrate 6a; and in which the optical prism 5 is optically adhered to a surface of the silica glass substrate 6a opposite to a surface on which the silicon oxide layer 6c is provided.

The optical prism 5 is set to have 43° or less of an angle between an incident surface on which light is incident through the polarizing plate 4 and an adhesion surface which adheres to the detection plate 6 (i.e., angle α in the figure). Such a setting can achieve a small-sized and highly sensitive detection device by complementing a difference between a condition for exciting SPR in conventional SPR sensors and a condition for exciting optical waveguide mode in optical waveguide mode sensors.

When measuring properties of the incident light reflected by the detection plate 6 (e.g., a spectrum of reflected light) using the detection device 50 having the above-described configuration, a certain wavelength range in incident light meets a condition for exciting an optical waveguide mode which locally propagates in and near the silicon oxide layer 6c formed on the surface of the detection plate 6, which causes a phenomenon in which the reflection intensity is significantly weakened in the wavelength range. The condition for exciting an optical waveguide mode varies depending on the dielectric constant in the proximity of the surface of the silicon oxide layer 6c in the detection plate 6. Thus, when the dielectric constant in the proximity of the surface of the silicon oxide layer 6c changes, the reflection spectrum also changes. Accordingly, a cause of a change in the dielectric constant in the proximity of a surface of the silicon oxide layer 6c (e.g., adsorption, desorption, access, or change in property of substances) can be detected with photodetector 9 by measuring a change in the reflection spectrum or a change in the intensity of reflected light within a certain wavelength range.

EXAMPLES

Figure 9:
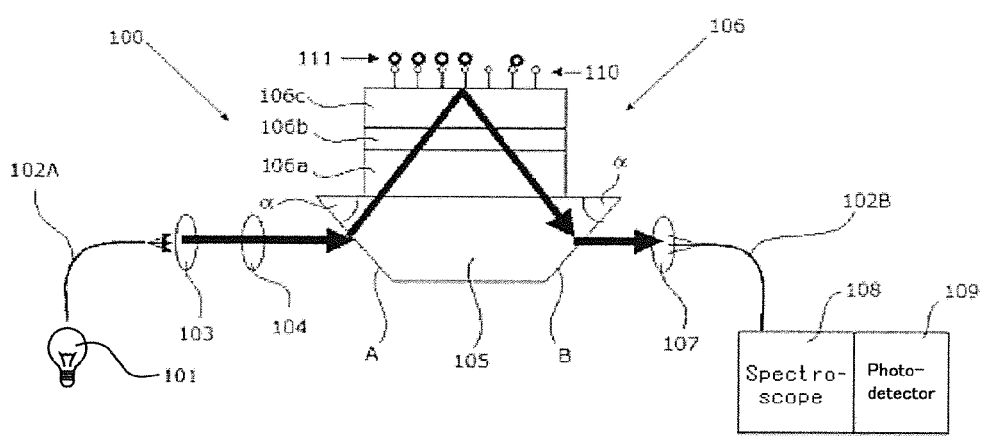
FIG. 9 illustrates an explanatory schematic view of a detection device according to Example of the present invention.

FIG. 9 illustrates a schematic view of a detection device 100 according to Example of the present invention. In this detection device 100, light irradiated from the tungsten-halogen lamp 101 is sequentially introduced, via the optical fiber 102A, to the collimator lens 103 and the polarizing plate 104 in this order, made into s-polarized collimated light, and then irradiated to the prism 105. The detection plate 106 is optically adhered to the prism 105. Here, a trapezoidal prism in which both of two base angles α were 38° was used as the prism 105. As the detection plate 106, there was used a detection plate in which the single crystal Si layer 106b having the thickness of 220 nm and the thermal-oxidized silicon layer 106c having the thickness of 448 nm were arranged in this order on the silica glass substrate 106a having the thickness of 1.2 mm.

The detection device 100 was made so that light irradiated, through the light incident surface A of the prism 105, to the detection plate 106 was reflected by the detection plate and then exited from the light exit surface B of the prism 105, followed by being directed to the spectroscope 108 equipped with the CCD array through the condensing lens 107 and the optical fiber 102B and being measured for the spectrum using the photodetector 109.

The detection test for specific adsorption between biotin 110 and streptavidin 111 was performed using the detection device 100 according to this Example as follows.

At first, the detection plate 106 was immersed in a weak alkaline aqueous solution for 10 hours and dried, followed by immersing in a 0.2% by mass solution of 3-aminopropyltriethoxysilane in ethanol for 10 hours to thereby modify the surface of the silicon oxide layer 106c with reactive amino groups.

The resultant is rinsed with ethanol and dried, followed by immersing in 1/15 M phosphate buffer containing 0.1 mM of sulfosuccinimidyl-N-(D-biotinyl)-6-aminohexanate (succinimide group-containing compound). After standing for 5 hours, amino groups were allowed to react with succinimide groups in the succinimide group-containing compound to thereby introduce biotinyl groups onto the surface of the silicon oxide layer 106c. As described above, the specific adsorption of streptavidin to biotinyl groups can be measured.

Specifically, biotinyl groups were introduced onto the silicon oxide surface 106c according to the above method, a liquid cell was mounted on the resultant modified silicon oxide surface 106c. The liquid cell was filled with 1/15 M phosphate buffer, and then the detection device 100 was driven to thereby measure the reflection spectrum by the photodetector 109. The measurement results are shown in FIG. 10 as a solid line.

Thereafter, the 1/15 M phosphate buffer was removed, the liquid cell was charged with fresh 1/15 M phosphate buffer containing 0.5 μM of streptavidin, and then the reflection spectrum was again measured. The measurement results are shown in FIG. 10 as a broken line.

Figure 10:
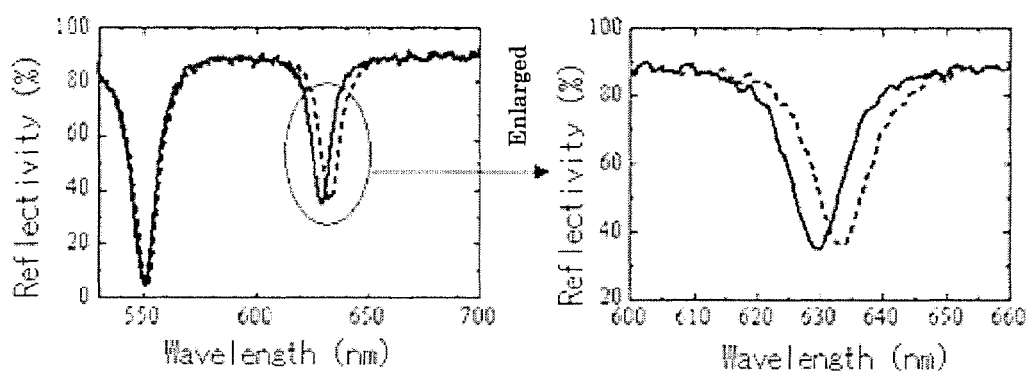
FIG. 10 illustrates spectra of reflected light measured by a detection device according to Example of the present invention.

As can be seen from FIG. 10, upon injecting the solution containing streptavidin, the adsorption reaction was occurred between the biotin 110 and the streptavidin 111, leading to a shift of the dip position seen in the reflection spectrum toward longer-wavelength side.

A setting which allows a wavelength shift amount of a dip position as seen in FIG. 10 occurred when the dielectric constant changes in the proximity of the surface of the detection plate 106 to be larger can provide a higher sensitive detection of a change in the dielectric constant and thus a more reliable detection of a reaction causing the change in the dielectric constant. Thus, the simulation calculation was performed for a relationship between an angle α of a prism and a wavelength shift amount of a dip position. For the above simulation calculation, a calculation computer program based on Fresnel equations and the freeware computer program WINSPALL (Wolfgang Knoll's group, MPI-P) were used.

For the above simulation calculation, the following 4 conditions were used: (1) the case in which a thickness of a silicon layer in a detection plate was 45 nm, and a bottom of a dip was at 600 nm of incident wavelength; (2) the case in which the thickness of the silicon layer in the detection plate was 80 nm, and the bottom of the dip was at 470 nm of incident wavelength; (3) the case in which the thickness of the silicon layer in the detection plate was 160 nm, and the bottom of a the dip was at 520 nm of incident wavelength; and (4) the case in which the thickness of the silicon layer in the detection plate was 220 nm, and the bottom of the dip was at 650 nm of incident wavelength. In any cases, the calculations were performed assuming that the silicon layer was formed from single crystal silicon.

In addition, the calculations were performed assuming that the surface of the detection plate 106 was immersed in a liquid having the refractive index equivalent to that of water, and the silicon oxide layer 106c was formed from silica glass. The thickness of the silicon oxide layer 106c affects a wavelength position at which a dip appears. Therefore, the thicknesses of the silicon oxide layers were set so that the dip positions were present at the above-described wavelengths in a state in which the surface of the detection plate is submerged in the liquid. The shift amounts of the dip positions were calculated assuming that a substance having the refractive index of 1.45 was adsorbed onto the surface of the detection plate 106 in the thickness of 5 nm.

Figure 11:
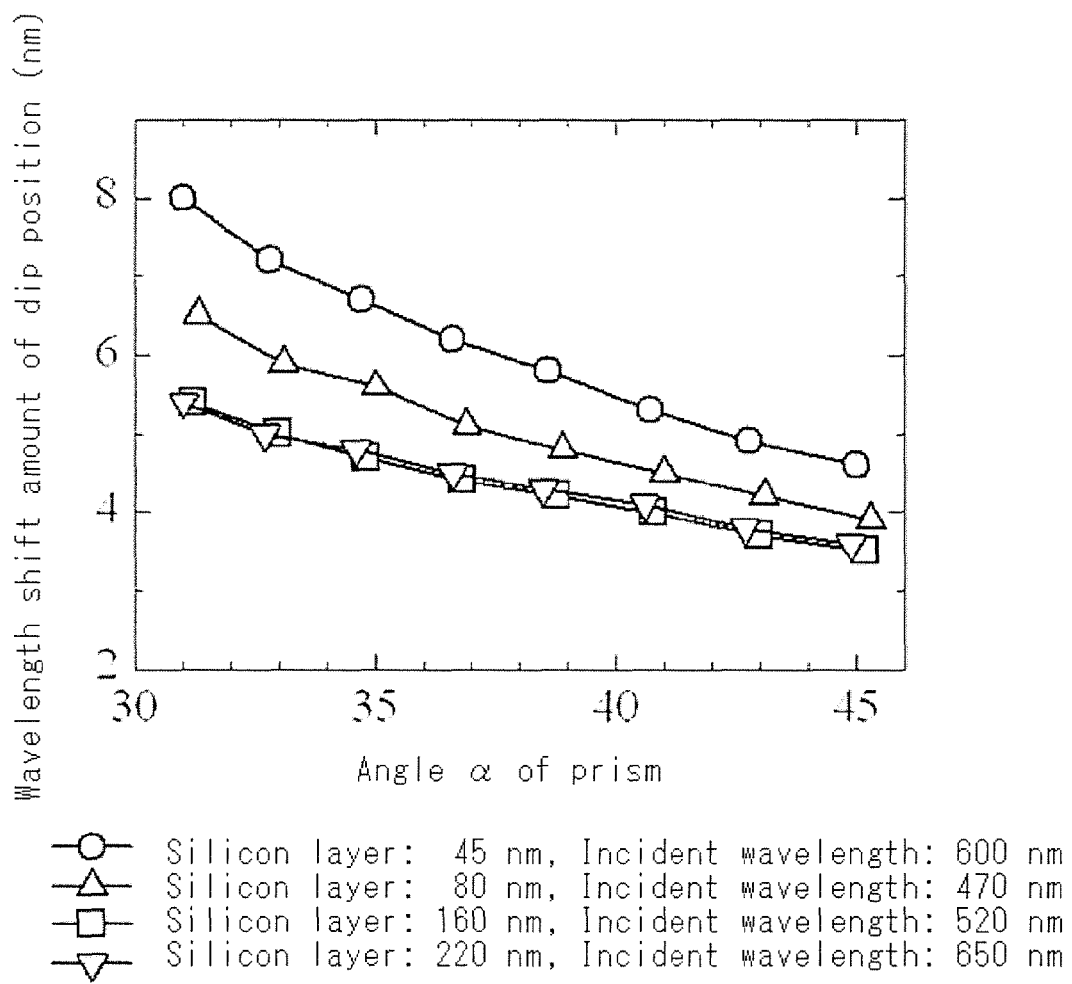
FIG. 11 illustrates a relationship between shift amounts of dip positions in reflected light spectra and angles of prisms calculated using configuration settings of a detection device according to Examples of the present invention.
Figure 12:
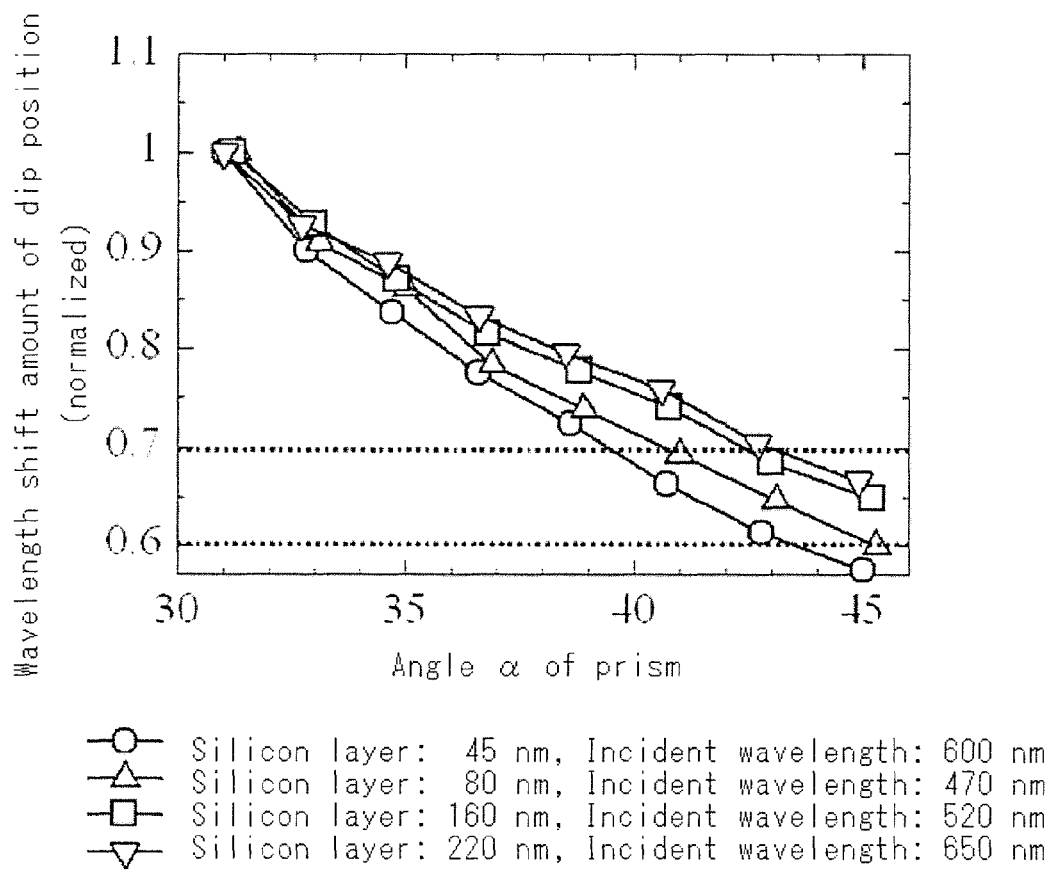
FIG. 12 illustrates a relationship between shift amounts of dip positions in reflected light spectra and angles of prisms calculated using configuration settings of a detection device according to Examples of the present invention.

The results obtained by the calculations are shown in FIG. 11 which demonstrates that a wavelength shift amount is dependent on an angle α of a prism. FIG. 12 shows the shift amounts normalized by the value when the angle α of the prism is 31°.

As shown in FIGS. 11 and 12, under the conditions used in the calculations, in any cases, the smaller the angle α of the prism is, the larger the shift amount is (that is, the higher the sensitivity is) regardless of differences in the thickness of the silicon layer in the detection plate 106 and the excitation wavelength range.

However, when the angle α of the prism is less than 30°, incident light cannot meet a condition under which total reflection occurs on the surface of the detection plate 106. That is, the incident angle of light to the surface of the detection plate 106 may be smaller than the critical angle. The refractive index of each of materials used in the detection plate 106 is dependent on a wavelength. Therefore, the angle α of the prism at which the incident angle of light to the surface of the detection plate is smaller than the critical angle cannot be determined uniquely. However, it should be noted that optical wave guide mode is not excited when the incident angle of light is smaller than the critical angle.

Assuming that the shift amounts normalized by the value when the angle α of the prism is 31° are ideal values, the ideal values were compared with the shift amounts when angle α of the prism is other than 31°. When the angle α of the prism is 43° or less, under any conditions the calculations were performed, shift amounts of dip positions were 60% or more relative to that of when the angle α of the prism was 31° (see FIG. 12). Therefore, 43° or less of the angle α of the prism can achieve high sensitivity upon adapting the $SiO_2/Si/SiO_2$ detection plate and the spectral measurement method.

When the angle α of the prism is 41° or less, under any conditions the calculations were performed, the shift amounts of dip positions were about 70% or more relative to that of when the angle α of the prism was 31° (see FIG. 12), which are more preferable.

Industrial Applicability

The detection device of the present invention is a small-sized, highly stable, and highly sensitive detection device. Therefore, it can be applied to biosensors for DNA, proteins (e.g., antigens, or antibodies) or sugar chains; chemicalsensors for metal ions or organic molecules; and thermometers. In addition, it can be utilized in a wide range of field such as medical, drug development, food, or environment.

REFERENCE SIGNS LIST

1, 101, 204, 301, 403: Light source
2A, 2B, 102A, 102B, 302A, 302B: Optical fiber
3, 103, 304: Collimator lens
4, 104, 205, 305, 404: Polarizing plate
5, 105, 203, 303, 402: Optical prism
6, 106, 401: Detection plate
6a, 106a: Silica glass substrate
6b, 16b, 106b: Silicon layer
6c, 16c, 106c: Silicon oxide layer
7, 107, 308: Condensing lens
8, 108, 309A: Spectroscope
9, 109, 206, 309, 405: Photodetector
16a: Optical prism-shaped silica glass substrate
110: Biotin
111: Streptavidin
50, 100: Detection device
200, 300: SPR sensor
400: Optical waveguide mode sensor
201, 306: Glass substrate
202, 307: Thin metal layer
210A, 310A, 410A: Incident light
210B, 310B, 410B: Exit light
401a: Transparent substrate
401b: Reflection layer
401c: Transparent optical waveguide layer

The invention claimed is:

1. A detection device, comprising:
   a detection plate comprising a silicon oxide layer, a silicon layer, and a silica glass substrate in the stated order from the top;
   an optical prism which is optically adhered to a surface of the silica glass substrate of the detection plate, where the surface is not provided with the silicon layer and the silicon oxide layer;
   a light-irradiation unit configured to irradiate light to the detection plate through the optical prism and arranged so that light is incident on the optical prism with a fixed incident angle; and
   a light-detection unit configured to detect intensity of reflected light reflected from the detection plate;
      wherein the detection device detects a change in dielectric constant in the proximity of the surface of the silicon oxide layer of the detection plate by detecting a change in property of the reflected light, and
   wherein in the optical prism, an angle between an incident surface on which light irradiated from the light-irradiation unit is incident and an adhesion surface which adheres to the detection plate is 43° or less.

2. The detection device according to claim 1, wherein the light-irradiation unit irradiates light in parallel with an in-plane direction of the adhesion surface.

3. The detection device according to claim 1, where the silicon layer is formed from a single crystal silicon.

4. The detection device according to claim 1, wherein an interface roughness between the silicon layer and the silicon oxide layer is 0.5 nm or less as a RMS value.

5. The detection device according to claim 1, wherein the light-irradiation unit comprises a light source, a collimator configured to collimate light irradiated from the light source to form collimated light, and a polarizing plate configured to polarize the collimated light into s-polarized light, and where the light-irradiation unit irradiates the s-polarized light to the detection plate through the optical prism.

6. The detection device according to claim 1, wherein the light-detection unit comprises a spectroscope configured to spectroscopically disperse and detect the reflected light.

7. The detection device according claim 1, where the optical prism has an exit surface which forms the same angle to the adhesion surface as that of the incident surface.

8. The detection device according to claim 1, wherein the optical prism is formed from silica glass having the same refractive index as that of the silica glass substrate.

9. The detection device according to claim 1, wherein the optical prism and the detection plate are integrally formed.

10. The detection device according to claim 1, wherein any of adsorption, desorption access, or change in property of a substance in the proximity of a surface of the silicon oxide layer is detected as a change in dielectric constant.

11. A detection device according to claim 1 wherein the angle between the incident surface and the adhesion surface is between 30° and 43°.

* * * * *